(12) United States Patent
Chiesi et al.

(10) Patent No.: US 6,297,237 B1
(45) Date of Patent: Oct. 2, 2001

(54) PROCESS FOR THE PREPARATION OF AMINOCARBONYL DERIVATIVES OF GENESEROLINE HAVING SELECTIVE BRAIN ANTICHOLINESTERASE ACTIVITY

(75) Inventors: Paolo Chiesi; Paolo Ventura; Vittorino Servadio; Roberto Pighi; Fausto Pivetti; Bluetta Salsi; Maurizio Delcanale; Gabriele Amari; Claudio Pietra, all of Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 09/319,693

(22) PCT Filed: Oct. 7, 1998

(86) PCT No.: PCT/EP98/06377

§ 371 Date: Aug. 2, 1999

§ 102(e) Date: Aug. 2, 1999

(87) PCT Pub. No.: WO99/19329

PCT Pub. Date: Apr. 22, 1999

(30) Foreign Application Priority Data

Oct. 10, 1997 (IT) ............................... MI97A2299
Oct. 10, 1997 (IT) ............................... MI97A2300

(51) Int. Cl.$^7$ ..................... A61K 31/5365; C07D 498/04
(52) U.S. Cl. .......................................... 514/229.8; 544/63
(58) Field of Search ............................ 544/63; 514/229.8

(56) References Cited

U.S. PATENT DOCUMENTS 5,538,968 * 7/1996 Chiesi et al. ...................... 514/229.8

FOREIGN PATENT DOCUMENTS

| 28 39 279 | 3/1979 | (DE) . |
| 0 253 372 | 1/1988 | (EP) . |
| WO 96 17828 | 6/1996 | (WO) . |

OTHER PUBLICATIONS

N. Node et al.: Chemical & Pharmaceutical Bulletin, vol. 44, No. 4, 1996, pp. 715–719, XP002092652 see p. 715, left-–hand column, compound 2.

P. L. Julian et al.: Journal of the American Chemical Society, vol. 57, 1935, pp. 755–757, XP002092654 cited in the application see p. 756, compound (VII) see p. 757, left–hand column, last paragraph to right–hand column, first paragraph.

E. Redenti et al.: Journal of Pharmaceutical Sciences, vol. 84, No. 9, Sep. 1995, pp. 1126–1133, XP002092653 see p. 1126, scheme 1; pp. 1126–1127, paragraph "Chemistry".

* cited by examiner

Primary Examiner—Richard L. Raymond
(74) Attorney, Agent, or Firm—Oblon, Spivak, McClelland, Maier & Neustadt, P.C.

(57) ABSTRACT

A process for the preparation of compounds of formula (I),

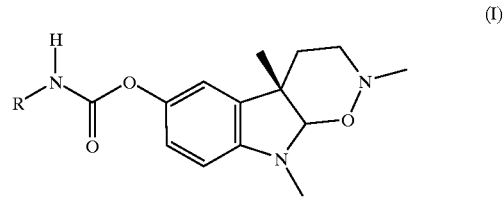

wherein R is $C_2$–$C_{20}$ linear or branched alkyl, $C_3$–$C_7$ cycloalkyl, phenyl or benzyl, which can optionally be substituted by $C_1$–$C_4$ alkyl, halogen or $C_1$–$C_4$ alkoxy group, said process comprising: a) oxidation of eserine with hydrogen peroxide in the presence of a base and subsequent hydrolysis to geneseroline, without isolating the intermediate geneserine; b) acylation of geneseroline with an isocyanate of formula R—N=C=O, wherein R is as defined above, in the presence of a basic catalyst; c) optional transformation into a pharmaceutically acceptable salt. Compounds of formula (I) wherein R is a phenyl or benzyl, which can be optionally substituted by alkyl, halogen or alkoxy, are selective, potent brain anticholinesterase inhibitors.

35 Claims, No Drawings

PROCESS FOR THE PREPARATION OF AMINOCARBONYL DERIVATIVES OF GENESEROLINE HAVING SELECTIVE BRAIN ANTICHOLINESTERASE ACTIVITY

This application is a 371 of International Application PCT/EP98/06377, filed Oct. 7, 1998.

DESCRIPTION

The present invention relates to a process for the preparation of structural analogues of geneseroline, in particular to aminocarbonyl derivatives of geneseroline of formula (I):

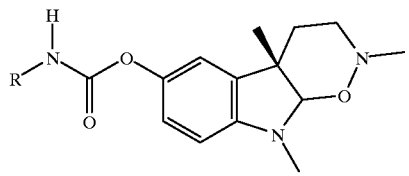

wherein R is $C_2$–$C_{20}$ linear or branched alkyl, $C_3$–$C_7$ cycloalkyl, phenyl or benzyl, which can optionally be substituted by $C_1$–$C_4$ alkyl, halogen or $C_1$–$C_4$ alkoxy group.

BACKGROUND OF THE INVENTION

Geneseroline derivatives of the above formula (I), having anticholinesterase activity, are disclosed in the European patent 0599890, in the name of Chiesi. These compounds can be used in the treatment of disorders of central nervous system.

The examples of preparation of the compounds of formula (I), as disclosed in the above patent, comprise the following steps:

a) hydrolysis of eserine to eseroline;

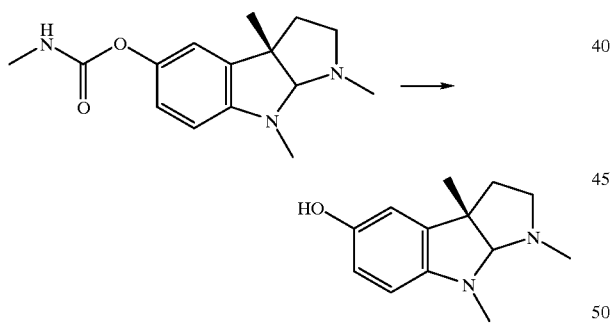

b) O-acylation of eseroline with reagents capable of introducing the desired function —CO—NHR, wherein R is as above defined;
c) oxidation of the so obtained eseroline aminocarbonyl derivatives to give the corresponding aminocarbonyl derivatives of geneseroline.

More specifically, in the examples of the patent, the preparation of only n-heptylaminocarbonylgeneseroline is disclosed.

Substituted imidazolureas or isocyanates are used for the acylation reaction.

Oxidation of eseroline derivatives to the corresponding geneseroline derivatives is carried out by using peracids or organic peroxides, such as m-chloroperbenzoic, monoperphthalic, peracetic acid, hydrogen peroxide, in inert solvents, such as halogenated hydrocarbons, aromatic hydrocarbons, dimethylformamide, dimethylsulfoxide.

Alternatively, the compounds of formula (I) have been prepared starting from geneseroline through hydrolysis of the methylaminocarbonyloxy group, and subsequent acylation, carried out by always using N-alkylimidazoleurea. Geneseroline is a well-known compound (Yu Q.S. et al. Journal of Natural Products, 52(2), 332–336, 1989).

The processes therein disclosed are unsuited to industrial scale, because of problems related to the cost of the starting alkaloid, reaction speed, yield and purity of the final product, due to side reactions.

It has now been found, and it is an object of the present invention, a process for the preparation of the compounds of formula (I), which is simple, economical, safe and applicable on industrial scale with good quantitative yields.

DISCLOSURE OF THE INVENTION

In a first embodiment of the present invention, the compounds of formula (I) can be prepared starting from eserine, according the following reaction scheme n.1, obtaining good yields, a good purity grade of the final product and improvement of reaction times.

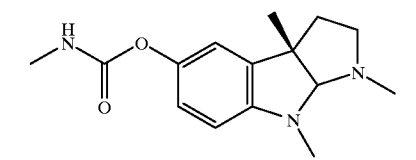

↓ a)

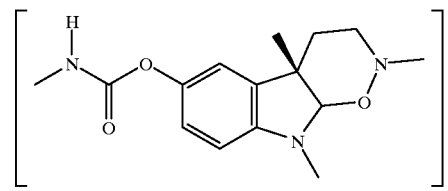

↓

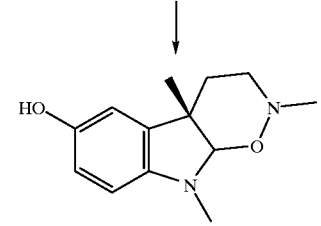

↓ b)

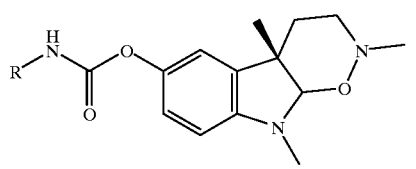

↓ c)

-continued

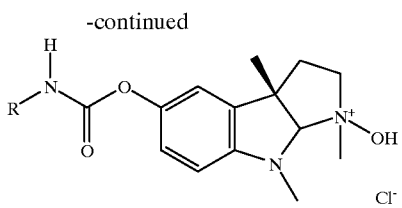

The process according to this first embodiment of the present invention comprises:

a) oxidation of eserine with hydrogen peroxide in the presence of a base and subsequent hydrolysis to geneseroline, without isolating the intermediate geneserine;

b) acylation of geneseroline with an isocyanate of formula R—N=C=O, wherein R is as defined in the above formula (I), in the presence of a basic catalyst;

c) optional transformation into a pharmaceutically acceptable salt.

The above disclosed process, comprising oxidation of eserine, followed by hydrolysis to geneseroline, without isolating the intermediate geneserine, allows a significant increase of the yields, maintaining a good purity of the final product.

Besides, the use of cheaper and less dangerous reagents makes the procedure more suitable for industrial scale.

Acylation reaction is carried out by using isocyanates according to classical methods, with a suitable basic catalyst, selected among alkali alcoholates, carbonates or hydroxides, such as potassium tert-butylate or potassium carbonate, the latter being particularly preferred for the application to industrial productions.

In order to speed up the process, the reaction may be carried out in the presence of small amounts of a phase transfer catalyst, such as tetrabutylammonium bromide, or using an ultrasound source.

In a second embodiment of the present invention, the synthesis is carried out by using as starting compounds ethers of formula (II)

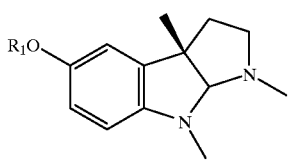

(II)

wherein $R_1$ is a protective group for phenolic hydroxyl, which must be stable in a basic environment and under strong reducing reaction conditions and can be removed in acidic conditions without reducing the geneserine-like N-oxide group. Examples of $R_1$ group are ethyl, tert-butyl, methoxymethyl, methoxyethoxymethyl, n-propyl, isopropyl, tetrahydropyranyl. This second embodiment of the present invention is carried out according to the following reaction scheme n.2, obtaining the compounds of formula (I) in three steps:

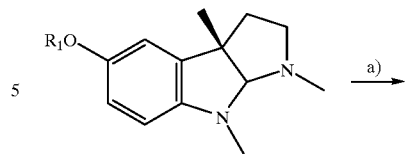

(II)

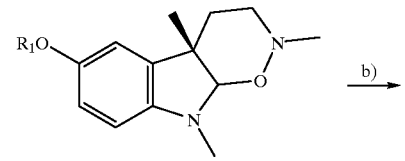

(III)

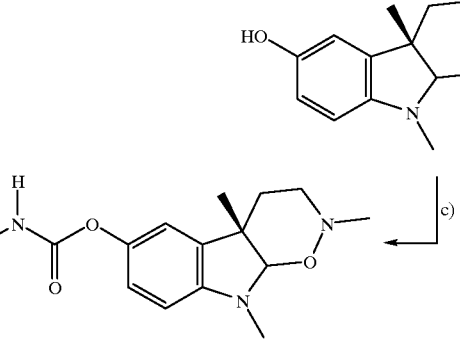

said process comprises:

a) oxidation of a compound of formula (II) with peracids or peroxides, preferably hydrogen peroxide, in an alcoholic solvent or in a water-alcohol mixture to give a compound of formula (III);

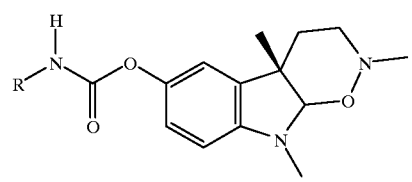

(III)

b) hydrolysis of the compound of formula (III) to geneseroline with a mineral acid or an organic acid, which does not reduce the N-oxide group;

c) acylation of geneseroline with an isocyanate of formula R—N=C=O, wherein R is as defined above and in the same reaction conditions disclosed for the process outlined in scheme 1 above;

d) optional transformation into a pharmaceutically acceptable salt.

For the purposes of the present invention, the definition of $R_1$ is clearly understood by the person skilled in this art, by resorting only to the general knowledge available in the pertaining literature, such as for example Greene, T. W., Wuts P. G. M. "Protective Groups in Organic Synthesis", 3, 145, Wiley, $2^{nd}$ edition 1990; Kocienski P. J. "Protecting Groups" 2, 21, Ed. Thieme 1994.

This process can be applied to both enantiomers of the ethers of formula (II), allowing obtaining both products with structure (I) and the corresponding enantiomers.

In a further embodiment of the present invention, compounds (I) can be prepared according to the following scheme 3

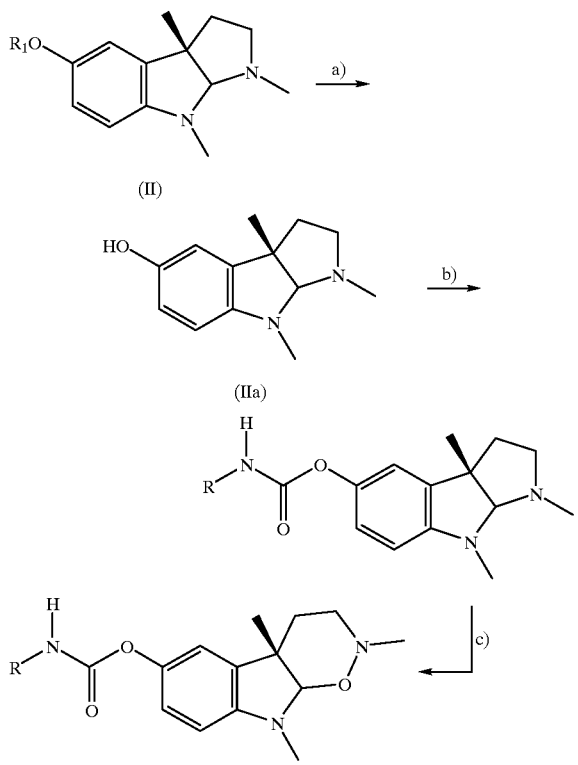

said process comprises:
a) hydrolysis with a mineral or an organic acid of a compound of formula (II)

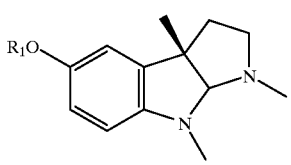

wherein $R_1$ is a protective group for the phenolic hydroxyl, which must be stable in a basic environment and under strong reducing reaction conditions and can be removed in acidic conditions, such as for example ethyl, tert-butyl, methoxymethyl, methoxyethoxymethyl, n-propyl, isopropyl, tetrahydropyranyl; to give eseroline (IIa)

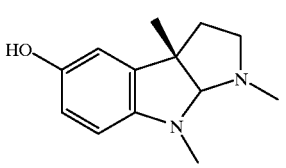

b) acylation of eseroline (IIa) with an isocyanate of formula R—N=C=O, wherein R is as defined above and in the same reaction conditions disclosed for the process outlined in scheme 1 above;

c) oxidation of the so obtained eseroline aminocarbonyl derivative to the corresponding geneseroline aminocarbonyl derivative;
d) optional transformation into a pharmaceutically acceptable salt.

Eseretole is one of the ethers that can be used in this invention and is commercially available at low cost and suitable quantities.

Other ethers, which proved to be particularly suited as starting compounds for the preparation of compounds (I), are for example:

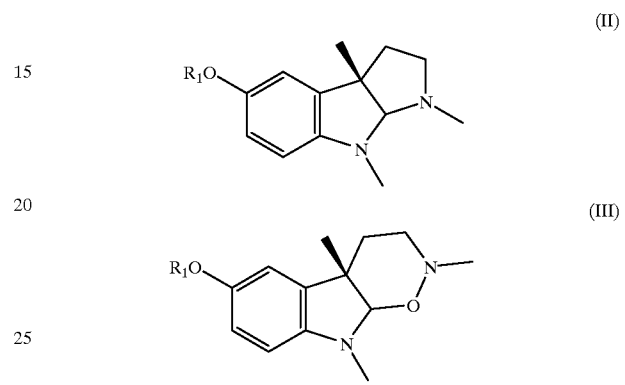

wherein $R_1$ is tert-butyl, methoxymethyl, methoxyethoxymethyl, n-propyl, isopropyl, tetrahydropyranyl.

These ethers may be prepared according to methods available in the literature.

Eseroline ethers of formula (II) and geneseroline ethers of formula (III), wherein $R_1$ is isopropyl, tert-butyl, methoxymethyl, and geneseroline ethers of formula (III) wherein $R_1$ is alkyl or alkoxylalkyl, among which tetrahydropyranyl are per se new, since they have never been disclosed before. Compounds (II) and (III) are within the scope of the present invention as intermediates in the process above disclosed.

The embodiments of the present invention according to the reaction schemes 2 and 3 are characterised by the step comprising the hydrolysis of eseroline ethers of formula (II) or geneseroline ethers of formula (III) to eseroline or geneseroline, respectively.

Technical literature provides many examples of hydrolysis of this kind of alkaloids, in particular esermetol and eseretole: Polonovsky M., Nitzerg C., Bull. Soc. Chim. Fr., 19, 33–37 (1916); Julian P., Pikl J., J. Am. Chem. Soc. 57, 755–757 (1935); Yu Q. S., Brossi A., Heterocycles, 27, 745–750 (1988).

However, in all the earlier documents, scientific papers and patents, hydrolysis of these ethers is carried out by using classical dealkylating agents, such as $BBr_3$, $BCl_3$, $AlCl_3$ (Lewis acids), HBr or other halogenhydric acids.

For example, U.S. Pat. No. 5310935 discloses the preparation of (3aS-cis)-eseroline by hydrolysing its methyl ether (or similar ethers) with $AlCl_3$ or $BBr_3$; International patent application WO 9427963 enables for the conversion of eseretole to physostigmin or its derivatives, according to the teaching by Julian P., Pikl J., J. Am. Chem. Soc. 57, 755–757 (1935); in European patent application n. 0253372 eseroline ether hydrolysis is carried out with $AlCl_3$ or $BBr_3$.

The application of the methods disclosed in the above references to the hydrolysis of the ethers of formula (III) to geneseroline did not give good results, since other reduction side reactions occur, with formation of unwanted by-products and consequent difficult purification of the obtained geneseroline and low yields. On the contrary, the method disclosed in the present invention allows to obtain highly pure geneseroline with good yields. The application of this method offers relevant work-and-cost effective advantages also in the presence of compounds of formula (II) with respect to Lewis acid uses.

A particular aspect of the present invention relates to the use of a mineral or organic acid for the hydrolysis of alkyl ethers of indole derivatives, such as for example eseroline, geneseroline or physovenol.

Suitable acids for the hydrolysis of compounds (II) or (III) are those having non-reducing properties, in particular with respect to compounds of formula (III), wherein the N—O group is sensitive to reducing agents. In the process according to the present invention, the acid is preferably selected from the group consisting of: sulfuric acid, phosphoric acid, hydrochloric acid, methanesulfonic acid, trifluoroacetic acid, acetic acid, a strongly acidic ion-exchange resin, such as Amberlyst®.

Hydrolysis conditions will be selected according to the $R_1$ group present in the molecule, in particular the choice will be made on the kind of acid, its concentration and hydrolysis temperature.

Sulfuric acid can be used at different concentrations from 10 to 85%, preferably at a temperature ranging from 50 to 90° C.

Phosphoric acid is generally used at the concentration of 85%, hot, preferably at a temperature of about 90° C.

Methanesulfonic acid is used as such and is made to react hot, preferably at a temperature of about 90° C.

Trifluoroacetic acid as such and 10% hydrochloric acid can be made to react warm at a temperature of about 40° C.

Compounds of formula (I) can be suitably transformed into their salts with pharmaceutically acceptable acids.

Derivatives of formula (I), similarly to their parent compound geneserine, when in the form of free base have a 1,2-oxazine structure, while in the respective salified forms they have a N-oxide structure (see Scheme 4)

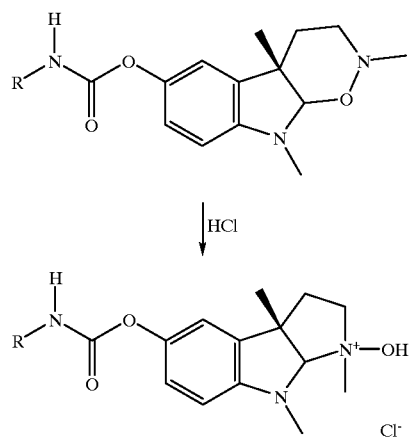

The process according to the present invention allows for the first time and contrarily to the process disclosed in EP 0599890 to prepare in industrial scale compounds of formula (I), in particular wherein R is an aromatic group, preferably phenyl and benzyl, optionally substituted by $C_1$–$C_4$ alkyl, halogen or $C_1$–$C_4$ alkoxy.

It has surprisingly been found that the compounds of formula (I), wherein R is an aromatic group, in particular phenyl and benzyl, optionally substituted by $C_1$–$C_4$ alkyl, halogen or $C_1$–$C_4$ alkoxy, have potent anticholinesterase activity, which is selective at cerebral level. These compounds, whose pharmacological properties were not effectively disclosed in EP 0599890, therefore represent a selection with respect to the earlier European patent and are a further object of the present invention.

In fact, European patent 0599890 relates to aminocarbonyl derivatives of geneseroline of formula (I):

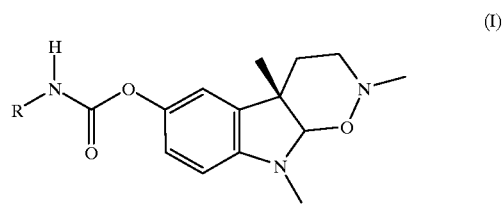

(I)

wherein R is $C_2$–$C_{20}$ linear or branched alkyl, $C_3$–$C_7$ cycloalkyl, phenyl or benzyl, which can optionally be substituted by $C_1$–$C_4$ alkyl, halogen or $C_1$–$C_4$ alkoxy group.

The teaching of this patent enables the pharmacological properties only of n-heptylaminocarbonylgeneseroline (named also CHF 2060), which is an inhibitor of brain acetylcholinesterase characterised by a long action.

Symptomatic therapy of senile dementia associated to Alzheimer disease can be done with substances having anticholinesterase activity, with the purpose to raise acetylcholine brain levels and restore cholinergic neurons functionality. Tacrine was the first compound endowed with these properties to come into clinical practice (Cognex; Davis K. L. et al., N. Eng. J. Med., 327: 1253–1259, 1993).

However, hepatic side effects and poor selectivity at central level of this product stimulated pharmacological research to find out new compounds having higher activity and higher selectivity of action toward central level. Briefly, there is the need to have available a compound having high anticholinesterase activity, long duration of action, higher affinity on acetylcholinesterase enzyme (AChE) with respect to butyrylcholinesterase (BuChE) and at the same time to be selective "in vivo" in inhibiting brain AChE with respect to the same enzyme present in other peripheral organs, for example in the heart.

SDZ-ENA 713 (commercial name Exelon), described in Enz A. et al. Progress in Brain Res. 98, 431–438, 1993, can be considered one of the selective anticholinesterase substances. This compound has been used by the applicant as comparison in some studies.

It has now been found that compounds of formula (Ia)

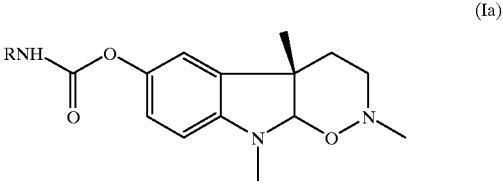

(Ia)

wherein R is phenyl or benzyl group, which can optionally be substituted by $C_1$–$C_4$ alkyl, halogen or $C_1$–$C_4$ alkoxy group are endowed with better pharmacological properties than the compounds of formula (I) wherein R is $C_2$–$C_{20}$ linear or branched alkyl, $C_3$–$C_7$ cycloalkyl, in particular n-heptyl.

Accordingly, the present invention further relates to compounds of formula (Ia) as new compounds when used as medicaments.

It is another object of the present invention compounds of formula (Ia) and their pharmaceutically acceptable salts.

Still another object of the present invention is a pharmaceutical composition containing a therapeutically effective amount of at least a compound of formula (Ia). The use of said compounds as active ingredient for the manufacture of a medicament is also within the scope of the present invention.

According this further aspect of the present invention, examples of phenyl or benzyl group substituted with $C_1$–C4 alkyl group are 2-methylphenyl, 3-methylphenyl, 4-methylphenyl, 2-methylbenzyl, 3-methylbenzyl, 4-methylbenzyl, 2-ethylphenyl, 3-ethylphenyl, 4-ethylphenyl, 2-ethylbenzyl, 3-ethylbenzyl, 4-ethylbenzyl, 2-propylphenyl, 3-propylphenyl, 4-propylphenyl, 2-propylbenzyl, 3-propylbenzyl, 4-propylbenzyl, 2-butylphenyl, 3-butylphenyl, 4-butylphenyl, 2-butylbenzyl, 3-butylbenzyl, 4-butylbenzyl, being intended that the terms propyl and butyl comprise both linear and branched isomers. Examples of phenyl or benzyl group substituted with halogen atoms are 2-chlorophenyl, 3-chlorophenyl, 4-chlorophenyl, 2-chlorobenzyl, 3-chlorobenzyl, 4-chlorobenzyl, 2-bromophenyl, 3-bromophenyl, 4-bromophenyl, 2-bromobenzyl, 3-bromobenzyl, 4-bromobenzyl, 2-iodiophenyl, 3-iodiophenyl, 4-iodiophenyl, 2-iodiobenzyl, 3-iodiobenzyl, 4-iodiobenzyl. Examples of phenyl or benzyl group substituted with $C_1$–C4 alkoxy group are 2-methoxyphenyl, 3-methoxyphenyl, 4-methoxyphenyl, 2-methoxybenzyl, 3-methoxybenzyl, 4-methoxybenzyl, 2-ethoxyphenyl, 3-ethoxyphenyl, 4-ethoxyphenyl, 2-ethoxybenzyl, 3-ethoxybenzyl, 4-ethoxybenzyl, 2-propoxyphenyl, 3-propoxyphenyl, 4-propoxyphenyl, 2-propoxybenzyl, 3-propoxybenzyl, 4-propoxybenzyl, 2-butoxyphenyl, 3-butoxyphenyl, 4-butoxyphenyl, 2-butoxybenzyl, 3-butoxybenzyl, 4-butoxybenzyl, being intended that the terms propoxy and butoxy comprise both linear and branched isomers.

Preferred compound according to the present invention are those in which R is selected from the group consisting of: 2-ethylphenyl (named also CHF2819), 3-methylphenyl (CHF 2957) and 2-methylphenyl (CHF 2822).

In a Declaration filed with United States Patent and Trademark Office, during the prosecution of U.S. Pat. No. 5,538,968, corresponding to EP 0599890, it was shown for the compounds of the present invention a particular selectivity with respect to brain acetylcholinesterase (AChE) in comparison with plasma acetylcholinesterase (AChE), therefore a higher selectivity for the brain than the one for the peripheral system.

It has now been found that aminocarbonyl derivatives of geneseroline of formula (Ia) show a higher inhibition potency for brain acetylcholinesterase (AChE) with respect to the derivatives substituted with an alkyl residue at the same position, such as disclosed in the above cited European patent and in particular to n-heptylgeneseroline. The potency increase observed occurs at the same efficacy of enzymatic inhibition. Besides, the compounds of formula (Ia) evidenced not only a higher potency, but also a higher selectivity of enzymatic inhibition. In fact, these compounds demonstrate both a higher selectivity at tissue level, (brain tissue with respect to heart tissue) and a higher selectivity for acetylcholinesterase (AChE) than butyrylcholinesterase (BuChE).

This selectivity is superior than the n-heptylgeneseroline one and to the reference compounds, such as physostigmine and SDZ-ENA 713.

The following examples further illustrate the invention.

EXAMPLE 1

Synthesis of geneseroline

Eserine (40 g, 0.1455 mol) was dissolved in 80 ml of methanol in a flask cooled to +10° C. with an ice bath. Potassium bicarbonate (14.5 g, 0.1455 mol) was added with vigorous stirring, then 35% (w/v) hydrogen peroxide (21.2 ml, 0.2182 mol) was dropped during 10 min.

The cooling bath was taken away and stirring was kept on for 2.5 hours.

An HPLC analysis showed eserine content to be lower than 1%. The solution was cooled again with an ice bath and 150 ml of 25% w/v NaCl solution were added.

Methanol was evaporated at reduced pressure, warming at a maximum temperature of 35° C. during about 10 min.

The aqueous phase was extracted three times with 150 ml of chloroform and the organic phases were evaporated at reduced pressure giving the crude geneserine as a foaming oily residue.

The crude residue was dissolved in 100 ml of 62% (w/w) sulfuric acid and the solution was quickly heated to 85° C. under a gentle flow of nitrogen. Heating was continued for 2 hours and an HPLC analysis showed a geneserine content lower than 1%.

The mixture was cooled at r.t. and poured into 100 g of ice.

Ammonium hydroxide, 30% w/w in water, (120 ml) was added dropwise with stirring, while the reaction temperature was controlled below 20–25° C. with a water bath. When pH was 4, then 250 ml of ethyl acetate were added. When the aqueous phase was almost neutral, a tar residue started to separate.

The aqueous phase was further extracted twice with 200 ml of ethyl acetate, the organic phases were combined, washed with 20% w/v sodium chloride solution (200 ml), dried over sodium sulfate, filtered and evaporated at reduced pressure. The residue was triturated in hexane (200 ml), about 100 ml of solvent were evaporated at reduced pressure and the obtained suspension was cooled at 5° C. and filtered.

The product was dried at 50° C. at reduced pressure, yielding 26.53 g (78%) of geneseroline.

m.p.(Buchi)=142.5–146 ° C. content (anhydrous titration) >98% purity (HPLC)>98% IR, Mass and NMR spectra confirm the expected product.

EXAMPLE 2

Synthesis of geneseroline a) Synthesis of geneseretole

Eseretole (92.5 g, 0.377 mol)was dissolved in methanol (185 ml), then potassium bicarbonate (37.7 g, 0.377 mol) was added and the mixture was stirred for 10 minutes. Afterwards, during about 10 minutes, 40% w/v hydrogen peroxide (48 ml, 0.566 mol) and 5 ml of water were added, while cooling the flask in a water bath.

The mixture was stirred for 3 hours during which temperature raised from 20° C. to 26° C. Eseretole conversion was regularly checked by HPLC analysis and the reaction was stopped when residual eseretole content was lower then 2%.

The mixture was poured under stirring in 750 ml of 25% w/v sodium chloride aqueous solution, then extracted with petroleum ether (1000+500+500 ml).

The yellow organic phase was washed with 20% w/v sodium chloride solution (200 ml), dried over anhydrous sodium sulfate, filtered and concentrated in a rotary evaporator. Evaporation was stopped when the residual solvent volume was about 150 ml. The so obtained suspension was stirred while cooling in an ice bath for 30 minutes and then filtered. The product was dried at 30° C. under vacuum, giving 72.04 g (73.2%) of geneseretole.

m.p.(Buchi)=78–80° C. content (titration on anhydrous)= 96% purity (HPLC)>98% $[\alpha]D^{20°}$ $^C$(0.5% in ethanol)=−177°.

b) Synthesis of aeneseroline

Geneseretole (71.9 g, 0.274 mol) was dissolved in 87.5% w/w sulfuric acid (250 ml) and the reddish solution was stirred and heated at 90° C.

The geneseretole conversion was followed through HPLC analysis and reaction was stopped after 3 hours when residual geneseretole content was about 3%.

The mixture was cooled with an ice bath and poured into ice (800 g) under stirring.

Then, 30% w/v ammonium hydroxide (500 ml) was slowly dropped in order to raise pH to 7.5, while keeping temperature <30° C. by adding some ice. When pH was about 5–6, ethyl acetate (1000 ml) was added to dissolve separated geneseroline.

The aqueous phase was extracted with further ethyl acetate (500+500 ml) and the organic phases were joined, washed with 20% w/v sodium chloride solution (500 ml), dried over anhydrous sodium sulfate and filtered.

The solution was concentrated in a rotary evaporator and when solid product began to precipitate, 600 ml of n-heptane were added in two successive portions and evaporation was continued until residual solvent volume was about 200 ml, in order to completely strip ethyl acetate.

The so obtained suspension was stirred while cooling at 5° C. during 30 minutes and then filtered and washed with petroleum ether. After drying at 50° C. under vacuum, 54.5 g (84.7%) geneseroline were obtained.

m.p.(Buchi)=143.5–145.5° C. purity (HPLC)>98% $[\alpha]D^{20}$(0.5% in ethanol)=−180°.

EXAMPLE 3

Hydrolysis of geneseroline ethers

With a procedure similar to the one of example 2b, geneseroline ethers of formula (III) were subjected to hydrolysis.

In the following Table the acids used, temperatures and reaction times are shown, together with the geneseroline yield, estimated as percent area in HPCL chromatogram of the crude product obtained.

TABLE

| $R_1$ | acid conc. (w/w) | Temperature (° C.) | reaction time (min) | geneseroline yield (%) |
|---|---|---|---|---|
| t-butyl | $H_2SO_4$ 87.5% | 90° C. | 10 | 99.3% |
| i-propyl | $H_2SO_4$ 87.5% | 90° C. | 10 | 73.9% |
| n-propyl | $H_2SO_4$ 87.5% | 90° C. | 10 | 76.7% |
| t-butyl | $H_2SO_4$ 62% | 90° C. | 5 | 100% |
| i-propyl | $H_2SO_4$ 62% | 90° C. | 15 | 96.3% |
| MOM | $H_2SO_4$ 16% | 90° C. | 15 | 69.8% |
| MEM | $H_2SO_4$ 16% | 90° C. | 15 | 71.7% |
| t-butyl | $H_2SO_4$ 16% | 90° C. | 15 | 92.4% |
| THP | $H_2SO_4$ 16% | 90° C. | 5 | 77.9% |
| MOM | $H_3PO_4$ 85% | 90° C. | 15 | 79.4% |
| MEM | $H_3PO_4$ 85% | 90° C. | 15 | 75.4% |
| t-butyl | $H_3PO_4$ 85% | 90° C. | 15 | 100% |
| i-propyl | $H_3PO_4$ 85% | 90° C. | 150 | 99.4% |

TABLE-continued

| $R_1$ | acid conc. (w/w) | Temperature (° C.) | reaction time (min) | geneseroline yield (%) |
|---|---|---|---|---|
| THP | $H_3PO_4$ 85% | 90° C. | 5 | 84.5% |
| t-butyl | MES | 90° C. | 15 | 100% |
| i-propyl | MES | 90° C. | 15 | 92.7% |
| t-butyl | TFA | 40° C. | 15 | 95.5% |
| MOM | TFA | 40° C. | 60 | 88.7% |
| MEM | TFA | 40° C. | 60 | 96.6% |
| THP | TFA | 40° C. | 5 | 83.0% |
| t-butyl | HCl 10% | 40° C. | 30 | 94.6% |
| MOM | HCl 10% | 40° C. | 30 | 91.3% |
| MEM | HCl 10% | 40° C. | 30 | 89.5% |
| THP | HCl 10% | 40° C. | 5 | 81.2% |
| THP | AcOH 90% | 40° C. | 120 | 80.0% |

Wherein: MOM: methoxymethyl, MEM: methoxyethoxymethyl, MES: methanesulfonic acid: TFA: trifluoroacetic acid, THP: tetrahydropyranyl, AcOH: acetic acid.

EXAMPLE 4

Eseroline synthesis through hydrolysis of eseretole

Eseretole (5g, 0.0203 mol) was dissolved in 87.5% w/w sulfuric acid (25 ml) and the solution was stirred at 90° C. up to complete conversion (75 min). The mixture was cooled and poured into ice. 30% ammonia (55 ml)was slowly added while cooling and keeping under nitrogen atmosphere up to pH=8. The aqueous phase was saturated with NaCl and extracted with ethyl ether (100+75+75 ml).

The organic phase, after washing with 20% w/v sodium chloride solution, drying over $Na_2SO_4$, was filtered and evaporated. A yellow oil, which solidified upon standing, was obtained. After drying under vacuum at r.t., eseroline weighed 3.04 g (70.6% yield)and its HPLC purity was 97%.

Other eseroline ethers of formula (II) can be subjected to hydrolysis with similar procedures to give eseroline. Once eseroline is obtained, geneseroline derivatives of formula (I) can be obtained according to examples 1 and 6 of the European patent 0599890.

EXAMPLE 5

Synthesis of n-heptylaminocarbonylgeneseroline

Geneseroline (73 g, 0.31 mol) was dissolved in ethyl acetate (1100 ml) at 37° C.

Potassium carbonate (11 g) was added to the clear solution and the suspension was stirred for 10 minutes.

Afterwards, heptylisocyanate (48 g) was dropped quickly, in 3–5 minutes. A slight heat development was observed and temperature raised to 47° C.

The reaction mixture was stirred for 3 hours, then 1 g of tetrabutylammonium bromide was added; a further addition of heptylisocyanate (4.3 g) reduced geneseroline content below 2%.

The reaction mixture was cooled, filtered through a celite pad and the clear solution was evaporated at reduced pressure.

To the brown oil obtained, toluene (400 ml) was twice added and the solution was evaporated at reduced pressure. The residue was dissolved in 600 ml of warm hexane and the solution obtained was cooled at 15° C. with stirring.

Precipitated n-heptylaminocarbonylgeneseroline was filtered, washed with hexane and dried at 50° C. under vacuum obtaining 102.7 g of crude product. The crude was suspended in 820 ml of water at room temperature for 30 min. with vigorous stirring, then filtered, washed with hexane and dried at 60° C. at reduced pressure to give 98.6 g (84.5%) of n-heptylaminocarbonylgeneseroline were obtained.

EXAMPLE 6

Synthesis of n-heptylaminocarbonylgeneseroline hydrochloride

N-heptylaminocarbonylgeneseroline (34.8 g, 0.093 mol) was dissolved in ethyl acetate (100 ml) at 40° C., then a solution of 22.5 ml of HCl 4.25 M in ethyl acetate diluted to 40 ml with the same solvent was dropped in. The solution was slowly cooled to 5° C., the product precipitated as a white solid that was filtered and dried at 60° C. at reduced pressure yielding 33.0 g of crude product.

The crude product was suspended in 165 ml of toluene at 40° C. and kept warm for 30 min. with stirring. The warm suspension was filtered, the solid was washed with toluene and diethyl ether, then dried at 60° C. at reduced pressure, giving 31.7 g (84%) of n-heptylaminocarbonylgeneseroline hydrochloride.

m.p.(Buchi)=147–148° C. content (titration on anhydrous >99% purity (HPLC) >99%.

The processes according to the present invention allow to obtain good yields also of compounds of formula (I) wherein R is an optionally substituted phenyl or benzyl group, starting from geneseroline and using a suitably substituted isocyanate as acylating agent.

EXAMPLE 7

Synthesis of n-(2-ethylphenyl) aminocarbonylgeneseroline hydrochloride

Potassium tert-butylate (112 mg, 1 mmol) is added to an ultrasonicated solution of geneseroline (2,34 g, 10 mmoles) and 2-ethylphenylisocyanate (1,61 g, 11 mmoles). After 3 minutes of ultrasonication, 11 mmoles of hydrochloric acid in ethyl acetate are added under magnetic stirring, the mixture is seeded with a small amount of product and stirring is continued for 2 hours. The so obtained crystalline product is filtered, washed with ethyl ether and dried u.v. at 40° C. 3,4 g (81.3%) of a white powder are obtained.

m.p.=179–181° C. $[\alpha]D^{20}(c=1, water)=-135°$.

Alternatively, n-(2-ethylphenyl) aminocarbonylgeneseroline hydrochloride can be obtained according to the method of the following example.

EXAMPLE 8

Synthesis of n-(2-ethylphenyl) aminocarbonylgeneseroline hydrochloride (CHF2819)

Geneseroline (75 g, 0.3 moles) was dissolved in acetone (750 ml), anhydrous potassium carbonate (2 g) was added and the mixture was stirred for 10 min.

Then a solution of 2-ethylphenylisocyanate (47.8 g, 0.324 mol) in acetone (100 ml) was slowly dropped in about 60 min while keeping T=20° C. After 30 min stirring, the suspension was filtered on a celite pad, washing with few acetone. The clear solution was concentrated to about 500 ml. The solution was added with 73 ml of a solution of 4.75M hydrochloric acid in ethyl acetate, while keeping T under 25° C.

After addition, temperature was lowered to 5° C., and after 120 minutes the suspension was filtered and washed with acetone (100 ml).

The so obtained solid was dried at 50° C. u.v. to constant weight, obtaining 106.04 g of raw product that, after crystallisation from absolute ethanol, gave 86.94 g (70.2%) of dry n-(2-ethylphenyl)amino-carbonylgeneseroline hydrochloride as white crystalline solid.

Melting point: 179–181.

With an analogous process and reacting geneseroline with a suitable isocyanate, the following compounds were prepared:

n-(3-methylphenyl)aminocarbonylgeneseroline hydrochloride (CHF2957) m.p.: 178.5–179.5° C.

n-(2-methylphenyl)aminocarbonylgeneseroline hydrochloride (CHF2822) m.p.: 172–174° C. (dec.).

In a preferred embodiment of the present invention, compounds CHF 2819, CHF 2957, CHF 2822 were evaluated for their enzymatic inhibition potency and selectivity of action through a series of parameters in comparison with n-heptylaminocarbonylgeneseroline hydrochloride (CHF2060).

Male SD rats weighing 150–200 g were split into groups of 8 animals each, depending on the treatment with the different substances, which were orally administered in distilled water, at a volume of 2 ml/kg. After 2 hours from the administration, the animals were sacrificed as to take their brains. Brain tissue was homogenized in a 11% Triton 100 solution in 0.1 M phosphate buffer at pH 8. After 15 minutes centrifugation, at 4° C., the supernatant was separated and AChE was determined on it with the method described by Ellman G. L. et al. (Biochem Pharmacol. 7, 88–95, 1961). For each treatment enzyme inhibition percent was determined against controls (animals treated with distilled water only).

Another series of experiments was performed in order to determine inhibition kinetics of brain and heart AChE after 1, 4 and 16 hours from administration of each tested substance. Enzyme was assayed on tissue homogenates similarly to what above described. The dose of each administered product corresponded to $\frac{1}{7}$ of its lethal dose ($LD_{50}$). Area Under Curve (AUC) was calculated by means of the enzymatic inhibition curve, for brain and heart tissue, related to the three test times.

The comparative results are reported in the following Table 1.

TABLE 1

| Compound | Dose mg/kg p.o. | Brain AChE inhibition (%) | $ED_{50}$ mg/kg p.o. (C.L. 95%) | Potency order (*) |
|---|---|---|---|---|
| CHF 2060 | 3 | 8 | 13.2 | 1 |
| | 10 | 29 | (5.9–26.6) | |
| | 30 | 60 | | |
| CHF 2819 | 0.4 | 9 | 1.5 | 8 |
| | 1.3 | 34 | (0.4–3.5) | |
| | 3.7 | 55 | | |
| CHF 2822 | 0.8 | 25 | 1.6 | 7 |
| | 2.5 | 46 | (0.6–3.1) | |
| | 7.5 | 68 | | |
| CHF 2957 | 3 | 21 | 4.1 | 3 |
| | 6 | 56 | (1.4–9.5) | |
| | 9 | 67 | | |

(*) $\frac{ED_{50} \text{ CHF 2060}}{ED_{50} \text{ compound}}$ n = 10

C.L. = Confidence Limits

From the consideration of the calculated $ED_{50}$ (dose of compound to inhibit 50% of the enzyme) values, it is evident that aryl derivatives are more potent than the reference compound CHF 2060 in inhibiting AChE after oral administration in rat. In particular, compound CHF 2819 resulted 8 times more potent than CHF 2060, while compounds CHF 2822 and CHF 2957 resulted 7 and 3 times more active, respectively. The analysis of enzymatic inhibition kinetics on brain tissue and heart homogenates is reported in the following Table 2.

TABLE 2

| Compound | dose (mg/kg p.o.) | brain AChE % inhibition | maximum Heart AChE | brain AUC (% inhib · xh) | Heart AUC (% inhib · xh) | selectivity index* |
|---|---|---|---|---|---|---|
| CHF 2060 | 10 | 20 | 41 | 252 | 450 | 0.6 |
| CHF 2819 | 1.3 | 32 | 4 | 348 | 36 | 9.7 |
| CHF 2822 | 2.5 | 45 | 9 | 379 | 96 | 3.9 |
| CHF 2957 | 9 | 62 | 13 | 585 | 125 | 4.7 |

*Brain AUC/Heart AUC n = 10

The results show that geneseroline aryl derivatives, differently from the alkyl derivatives, have a higher selectivity for brain with respect to heart tissue.

In a further series of experiments, compounds CHF 2819, CHF 2957 and CHF 2822 were evaluated in the "in vitro" inhibition of erythrocyte AChE and human plasma BuChE, in comparison with n-heptylaminocarbonylgeneseroline (CHF 2060) and the conventional cholinesterase inhibitors physostigmine and SDZ-ENA 713. The method used was similar to the one cited above, Ellman G. L. et al. The results are reported in Table 3.

TABLE 3

| Compound | AChE $IC_{50}$ ($\mu M$) ± s.e. | BuChE $IC_{50}$ ($\mu M$) ± s.e. | S.I. |
|---|---|---|---|
| Physostigmine | 0.18 ± 0.01 | 0.05 ± 0.004 | 0.27 |
| SDZ-ENA 713 | 57.9 ± 2.48 | 0.45 ± 0.02 | 0.007 |
| CHF 2060 | 0.85 ± 0.08 | 0.005 ± 0.0007 | 0.005 |
| CHF 2819 | 0.48 ± 0.06 | 55.2 ± 6.43 | 115 |
| CHF 2822 | 2.01 ± 0.08 | 0.18 ± 0.01 | 0.09 |
| CHF 2957 | 4.20 ± 0.29 | 133.8 ± 9.70 | 32 |

S.I. = selectivity index ($IC_{50}$ BuChE/$IC_{50}$ AChE) n = 4–8

All the tested compounds show an affinity (evaluated as $IC_{50}$, namely the concentration of compound to inhibit 50% of the enzyme) at micromolar level for AChE. Among these compounds, SDZ-ENA 713 is less active than other products. Significant differences came out in the inhibition of BuChE. In fact, CHF 2060, physostigmine and SDZ-ENA 713 are definitely more potent in inhibiting BuChE, rather than AChE. On the basis of the calculated selectivity indexes, compound CHF 2819 resulted to be 115 times more selective on AChE. Also CHF 2957 has a good selectivity, whereas CHF 2822 is slightly less selective.

It is well known that BuChE is mainly distributed in the peripheral tissue and, to a less extent, in the brain at the level of microglia. Therefore, the affinity shown by some of the tested compounds for this enzymatic form could explain their "in vivo" peripheral inhibitory activity.

From what explained in this invention, the compounds of formula (Ia) are useful for the preparation of a medicament having inhibiting activity of acetylcholinesterase. In particular, CHF 2819 is characterised, with respect to the other compounds herein taken into consideration, for a favourable "in vitro" selectivity on AChE with respect to BuChE, a good duration of action and an "in vivo" selectivity in inhibiting brain AChE.

In a preferred aspect of the present invention, said medicament is useful for the treatment of Alzheimer disease and other neurodegenerative pathologies.

Advantageously, this medicament is devoid of peripheral side effects and this feature is claimed in the present invention:

The medicament shall be formulated in forms and dosages that can be determined by the clinical expert in the field, depending on the kind of pathology, its severity and patient conditions.

As far as the aspects concerned with its industrial application, the present invention also provides pharmaceutical compositions comprising a therapeutically effective amount of active ingredient in admixture with carriers and excipients conventional in the pharmaceutical field.

Said compositions can be prepared with well known techniques, for example as described in "Remington's Pharmaceutical Sciences Handbook", Mack Pub., New York, U.S.A.

Examples of pharmaceutical compositions are oral forms, solid or liquid, such as tablets, capsules, solutions, suspensions, syrups; injectable forms, such as solutions, suspensions, emulsions; controlled release formulations.

The daily does of active ingredient to be administered with these compositions will range from 1 to 50 mg and preferably from 5 to 20 mg.

What is claimed is:

1. A process for the preparation of compounds of formula (I):

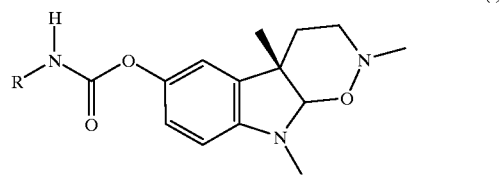

wherein R is $C_2$–$C_{20}$ linear or branched alkyl, $C_3$–$C_7$ cycloalkyl, phenyl or benzyl, which can optionally be substituted by $C_1$–$C_4$ alkyl, halogen or $C_1$–$C_4$ alkoxy group, said process comprising:

a) oxidation of eserine with hydrogen peroxide in the presence of a base and subsequent hydrolysis to geneseroline, without isolating the intermediate geneserine;

b) acylation of geneseroline with an isocyanate of formula R—N=C=O, wherein R is as defined above, in the presence of a basic catalyst;

c) optional transformation into a pharmaceutically acceptable salt.

2. A process according to claim 1, wherein the catalyst in step b) is selected from the group consisting of potassium tert-butylate and potassium carbonate.

3. A process according to claim 1, wherein in step b) a phase transfer catalyst is added.

4. A process according to claim 3, wherein tetrabutylammonium bromide is the phase transfer catalyst.

5. A process according to claim 1, wherein in step b) an ultrasonic source is used.

6. A process for the preparation of compounds of formula (I):

(I)

wherein R is $C_2$–$C_{20}$ linear or branched alkyl, $C_3$–$C_7$ cycloalkyl, phenyl or benzyl, which can optionally be substituted by $C_1$–$C_4$ alkyl, halogen or $C_1$–$C_4$ alkoxy group, said process comprising:

a) oxidation of a compound of formula (II) with peracids or peroxides (II)

wherein $R_1$ is a protective group for the phenolic hydroxyl, which must be stable in a basic environment and under strong reducing reaction conditions and can be removed in acidic conditions without reducing the geneserino-like N-oxide group, in an alcoholic solvent or in a water-alcohol mixture to give a compound of formula (III);

(III)

b) hydrolysis of the compound of formula (III) to geneseroline with a mineral acid or an organic acid, which does not reduce the N-oxide group;

c) acylation of geneseroline with an isocyanate of formula R—N=C=O, wherein R is as defined above, in the presence of a basic catalyst selected from the group consisting of alkali alcoholates, carbonates or hydroxides;

d) optional transformation into a pharmaceutically acceptable salt.

7. A process for the preparation of compounds of formula (I):

(I)

wherein R is $C_2$–$C_{20}$ linear or branched alkyl, $C_3$–$C_7$ cycloalkyl, phenyl or benzyl, which can optionally be substituted by $C_1$–$C_4$ alkyl, halogen or $C_1$–C4 alkoxy group, said process comprising a) hydrolysis of a compound of formula (II)

(II)

wherein $R_1$ is a protective group for the phenolic hydroxyl, which must be stable in a basic environment and under strong reducing reaction conditions and can be removed in acidic conditions to give eseroline of formula (IIa);

(IIa)

b) acylation of eseroline (IIa) with an isocyanate of formula R—N=C=O, wherein R is as defined above in the presence of a basic catalyst selected from the group consisting of alkali alcoholates, carbonates or hydroxides;

c) oxidation of the so obtained eseroline aminocarbonyl derivative to the corresponding aminocarbonyl derivative of geneseroline;

d) optional transformation into a pharmaceutically acceptable salt.

8. A process according to claim 6, wherein hydrolysis of compound (II) or (III) is carried out with an acid selected from the group consisting of sulfuric acid, phosphoric acid, hydrochloric acid, methanesulfonic acid, trifluoroacetic acid, acetic acid, a strongly acidic ion-exchange resin.

9. A process according to claim 6, wherein hydrolysis is carried out with sulfuric acid at a concentration ranging from 10 to 85% w/w.

10. A process according to claim 6, wherein hydrolysis is carried out with hot 85% w/w phosphoric acid.

11. A process according to claim 6, wherein hydrolysis is carried out with methanesulfonic acid at 90° C.

12. A process according to claim 6, wherein hydrolysis is carried out with hot trifluoroacetic acid or 10% hydrochloric acid at 40° C.

13. A process according to claim 6, wherein hydrolysis is carried out with a strongly acidic ion-exchange resin.

14. A process according to claim 6, wherein, in the acylation step, the basic catalyst is added with a phase transfer catalyst or an ultrasound source is used.

15. A process according to claim 7, wherein hydrolysis of compound (II) or (III) is carried out with an acid selected from the group consisting of sulfuric acid, phosphoric acid, hydrochloric acid, methanesulfonic acid, trifluoroacetic acid, acetic acid, and a strongly acidic ion-exchange resin.

16. A process according to claim 7, wherein hydrolysis is carried out with sulfuric acid at a concentration ranging from 10 to 85% w/w.

17. A process according to claim 7, wherein hydrolysis is carried out with hot 85% w/w phosphoric acid.

18. A process according to claim 7, wherein hydrolysis is carried out with methanesulfonic acid at 90° C.

19. A process according to claim 7, wherein hydrolysis is carried out with hot trifluoroacetic acid or 10% hydrochloric acid at 40° C.

20. A process according to claim 7, wherein hydrolysis is carried out with a strongly acidic ion-exchange resin.

21. A process according to claim 7, wherein, in the acylation step, the basic catalyst is added with a phase transfer catalyst or an ultrasound source is used.

22. Compounds of formula (Ia)

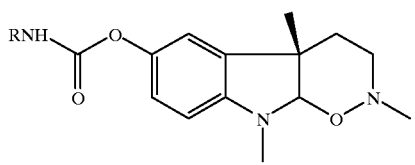

(Ia)

wherein R is phenyl or benzyl group, which can optionally be substituted by $C_1$–$C_4$ alkyl, halogen or $C_1$–$C_4$ alkoxy group and their pharmaceutically acceptable salts.

23. Compounds according to claim 22, wherein R is selected from the group consisting of 2-ethylphenyl, 3-methylphenyl, 2-methylphenyl.

24. The compound of claim 22, wherein R is 2-ethylphenyl.

25. Pharmaceutical compositions containing an effective amount of a compound of claim 22 in admixture with pharmaceutically acceptable carriers and excipients.

26. A method of inhibiting acetylcholinesterase activity in a patient comprising administering to said patient an effective amount of the compound of claim 22 to inhibit acetylcholinesterase activity.

27. A method of treating neurodegenerative disease in a patient in need thereof comprising administering to said patient an effect amount of the compound of claim 22 to treat a neurodegenerative disease.

28. The method of claim 27, wherein said neurodegenerative disease is Alzheimer's disease.

29. A method of inhibiting acetylcholinesterase activity in a patient comprising administering to said patient an effective amount of the compound of claim 24 to inhibit acetylcholinesterase activity.

30. A method of treating neurodegenerative disease in a patient in need thereof comprising administering to said patient an effect amount of the compound of claim 24 to treat a neurodegenerative disease.

31. The method of claim 30, wherein said neurodegenerative disease is Alzheimer's disease.

32. The method of claim 27, wherein said effective amount is from 1 to 50 mg per day.

33. The method of claim 32, wherein said effective amount is from 5 to 20 mg per day.

34. The method of claim 30, wherein said effective amount is from 1 to 50 mg per day.

35. The method of claim 34, wherein said effective amount is from 5 to 20 mg per day.

* * * * *